United States Patent
Patton

(10) Patent No.: US 9,828,707 B2
(45) Date of Patent: Nov. 28, 2017

(54) PARASITIC ACARI BARRIER

(71) Applicant: Lymeez LLC, Sedona, AZ (US)

(72) Inventor: John Patton, Sedona, AZ (US)

(73) Assignee: Lymeez LLC, Sedona, AZ (US)

( * ) Notice: Subject to any disclaimer, the term of this patent is extended or adjusted under 35 U.S.C. 154(b) by 0 days.

(21) Appl. No.: 15/360,510

(22) Filed: Nov. 23, 2016

(65) Prior Publication Data

US 2017/0143051 A1 May 25, 2017

Related U.S. Application Data

(60) Provisional application No. 62/259,979, filed on Nov. 25, 2015.

(51) Int. Cl.
| | |
|---|---|
| *D04B 21/10* | (2006.01) |
| *A41D 13/00* | (2006.01) |
| *B32B 5/02* | (2006.01) |
| *D04B 23/02* | (2006.01) |
| *A41D 17/04* | (2006.01) |

(52) U.S. Cl.
CPC ........... *D04B 21/10* (2013.01); *A41D 13/001* (2013.01); *A41D 17/04* (2013.01); *B32B 5/026* (2013.01); *B32B 5/028* (2013.01); *D04B 23/02* (2013.01)

(58) Field of Classification Search
CPC ...... A41D 13/05; A41D 13/001; A41D 31/02; A41D 17/04; D04B 21/10; D04B 21/207; D04B 23/16; D04B 23/02; D03D 11/02; B32B 5/028; B32B 5/026

See application file for complete search history.

(56) References Cited

U.S. PATENT DOCUMENTS

| | | | | |
|---|---|---|---|---|
| 2,344,811 A | * | 3/1944 | Gill | A41D 13/001 2/173 |
| 2,630,619 A | * | 3/1953 | Schmidt | A41H 41/005 28/162 |
| 3,783,451 A | * | 1/1974 | Malin | A41D 13/001 2/4 |
| 4,716,594 A | * | 1/1988 | Shannon | A41D 13/001 2/4 |
| 5,214,797 A | * | 6/1993 | Tisdale | A41D 13/001 2/4 |

(Continued)

OTHER PUBLICATIONS

International Search Report and Written Opinion for PCT/US2016/063548 dated Feb. 6, 2017 (8 pages).

(Continued)

*Primary Examiner* — Danny Worrell
(74) *Attorney, Agent, or Firm* — Shumaker, Loop & Kendrick, LLP

(57) ABSTRACT

A parasitic Acari barrier fabric that impedes parasitic Acari movement, traps parasitic Acari, and/or exterminates parasitic Acari thereon or therein. The barrier fabric includes an outer face formed from open mesh construction having evenly spaced openings formed thereon that are adapted for passing parasitic Acari from outside the fabric to inside the fabric, an inner face that is breathable and configured for moisture vapor transmission from a wearer's skin therethrough but is impenetrable to parasitic Acari passed to the inside of the fabric, and an intermediate spacer that extends between and interconnects the inner face to the outer face to form the parasitic Acari barrier fabric.

14 Claims, 8 Drawing Sheets

(56) References Cited

U.S. PATENT DOCUMENTS

| | | | | |
|---|---|---|---|---|
| 5,249,307 A * | 10/1993 | Lemoine | A41D 13/001 | 2/4 |
| 5,249,310 A * | 10/1993 | Forte | A41B 11/00 | 2/239 |
| 5,341,511 A * | 8/1994 | Wells | A41D 13/001 | 2/1 |
| 5,357,635 A * | 10/1994 | Lemoine | A41D 13/001 | 2/173 |
| 5,381,557 A * | 1/1995 | Luria | A01M 1/14 | 2/16 |
| 5,600,850 A * | 2/1997 | Shannon | A41D 13/001 | 2/4 |
| 5,794,263 A * | 8/1998 | Carman | A41D 13/001 | 2/202 |
| 6,141,802 A * | 11/2000 | Drake | A41D 1/08 | 2/22 |
| 6,199,217 B1 * | 3/2001 | Mooney | A41D 17/00 | 2/240 |
| 6,214,365 B1 * | 4/2001 | Shober | A01N 25/34 | 424/403 |
| 6,353,939 B1 * | 3/2002 | Arber | A41D 17/02 | 2/242 |
| 6,477,865 B1 * | 11/2002 | Matsumoto | D04B 1/02 | 66/195 |
| 6,716,774 B2 * | 4/2004 | Porter | A45F 3/52 | 119/850 |
| 6,728,969 B2 * | 5/2004 | Zeiler | A41D 13/001 | 2/4 |
| 6,802,082 B2 * | 10/2004 | Watley | A41D 13/001 | 2/900 |
| 7,140,048 B2 * | 11/2006 | Wallerstein | A41D 13/001 | 2/243.1 |
| 8,151,515 B2 * | 4/2012 | Crouse | A01M 3/04 | 43/132.1 |
| 8,240,174 B2 * | 8/2012 | Soeda | A41B 17/00 | 450/93 |
| 8,276,405 B2 * | 10/2012 | Ogata | D04B 1/16 | 66/171 |
| 8,316,672 B2 * | 11/2012 | Karatzis | D04B 21/12 | 66/170 |
| 8,906,398 B2 * | 12/2014 | Sonneck | A01N 25/10 | 424/403 |
| 9,532,615 B2 * | 1/2017 | Radefeldt | A41D 13/001 | |
| 2002/0088254 A1 * | 7/2002 | Singleton | A41B 11/00 | 66/177 |
| 2003/0106346 A1 * | 6/2003 | Matsumoto | D04B 1/10 | 66/195 |
| 2003/0198659 A1 * | 10/2003 | Hoffmann | A01N 25/34 | 424/411 |
| 2004/0112217 A1 | 6/2004 | Schroder | | |
| 2009/0004939 A1 * | 1/2009 | Graichen | D04B 1/12 | 442/49 |
| 2012/0330093 A1 | 12/2012 | Odermatt et al. | | |
| 2014/0007319 A1 | 1/2014 | Kuhl | | |
| 2014/0283560 A1 | 9/2014 | Patton et al. | | |
| 2014/0290123 A1 | 10/2014 | Duff | | |
| 2017/0143051 A1 * | 5/2017 | Patton | A41D 13/001 | |

OTHER PUBLICATIONS

International Search Report for PCT/US2016/063548 dated Feb. 6, 2017 (8 pgs.).

* cited by examiner

PARASITIC ACARI BARRIER

CROSS-REFERENCE TO RELATED APPLICATION

This application claims priority to U.S. Provisional Patent Application No. 62/259,979 filed Nov. 25, 2015, the contents of which are incorporated by reference herein in the entirety.

TECHNICAL FIELD

This invention relates to an Acari barrier including fabrics, gaiters, and putees that are worn to kill, repel, and/or enervate parasitic Acari. The Acarine gaiter allows the wearer to safely participate in outdoor activities in areas where parasitic Acari are present.

BACKGROUND

There are a considerable number of devices and prior art for preventing human (and/or mammalian) contact with flying insects, but very few devices and/or prior art exists for preventing human and mammalian contact with Acari. For combating flying insects the prior art discloses various devices and strategies including: (1) block, (2) block and hold away, and (3) block and poison.

For example, U.S. Pat. No. 5,794,263 discloses methods and devices for simply blocking flying insects. Prior representative flying insect patents with a simple blocking strategy further include U.S. Pat. No. 5,717,990 and U.S. Pat. No. 5,119,510. These references disclose devices that utilize netting to block, for example, mosquito contact. However, a drawback of these inventions is that the flying insects, in particular mosquitoes may continue to sting through the netting. Thus, these inventions are at least partially ineffective.

A second strategy for combating flying insects is to block the flying insects while simultaneously holding the blocking mechanism away from the human body. This strategy solves the above mentioned problem of mosquitoes stinging through the netting. U.S. Pat. No. 5,600,850 is representative of this approach. A similar "block and hold away" strategy is disclosed in U.S. Patent Application No. 2006/0048291 and U.S. Pat. No. 7,243,375. It is notable that both U.S. Pat. No. 7,080,412 and U.S. Patent Application No. 2013/0232676 use spacer fabric(s) as the method to hold the blocking mechanism away from the body. Here, the spacer fabric serves as a breathable spacer layer that is effective in preventing mosquitoes from stinging through the net.

A third strategy for combating flying insects is "block and poison" as disclosed in U.S. Patent Application No. 2013/0291275 (Radefeldt). Similar to Radefeldt, yet exclusively targeting the *Ixodes* genus of Acari, is U.S. Pat. No. 6,141,802 (Drake). Drake teaches a tick barrier system for a pair of pants. The pants have an integral inner gaiter that fits snugly around the wearer's ankle and are stitched to the inside of the pant leg. The prevention strategy is to prevent Ixodae contact with the wearer's skin by creating a cavity where the Ixodae are frustrated in their attempt to find skin. Presumably the Ixodae never find the path up the outside of the pant leg and either drop off or are removed after careful post-wear inspection. Drake, similar to Radefeldt, has an impede-and-divert approach absent the poison aspect of Radefeldt.

There are many similar drawbacks to Radefeldt and Drake in combating Acari. The primary problem is that questing Ixodae, generally traverse from a height of 2 to 8 inches off the ground, and therefore will easily climb onto the exterior of the pant leg, avoiding altogether the impede-divert mechanism of the inner pant legs. The pant legs of Radefeldt and Drake will do little to stop questing Acari from climbing onto the respective garments. Furthermore, and again from the perspective of the present invention, these garments, aside from the fundamental flaw of providing a convenient way for Ixodae to climb on to the outside of the garment, and while they are designed to be durable, also fail in being easy to use, comfortable, attractive and inexpensive for the user simply looking to avoid parasitic Acari.

U.S. Pat. No. 6,353,939 (Arber), like Drake, addresses directly the avoidance of the parasitic *Ixodes* genus of Acari. Arber teaches a disposable onetime use legging made of paper with upper and lower elastic bands that hold the Ixodae-repelling covering in place on the wearer's leg, for preventing bites by causing Ixodae to climb across externally mounted adhesive strips which capture them. The prevention strategy is that Ixodae will (1) climb onto the host from the foot and (2) will be captured by adhesive strips, and (3) will be rendered harmless when the device is disposed. It is a one time use item. It is intended to be worn with shoes or boots and with the wearer's legs covered. Again, considered from the perspective of the current invention, the trap-and-discard approach of Arber, while possibly effective for trapping Ixodae, fails in being easy to use, comfortable, durable, attractive, and inexpensive.

Finally, U.S. Patent Application No. 2014/0283560 (Patton) discloses an ixodicidally treated-knit sleeve (i.e., a poison only approach) to be used as a leg or forearm covering.

While the above discussed prior art, discloses methods and devices of diverting and/or killing flying insects (and in some instances Acari), more effective devices and methods of impeding Acari movement and/or killing Acari are needed, SUMMARY Disclosed is a parasitic Acari barrier fabric that provides a more effective approach for exposing Acari to greater amounts of acaricide as they traverse up the legs of wearers by impeding and diverting Acari movement with an impedimentary surface area of high wales and a diversionary field of deep pores attractive to exploration, backed by an impenetrable inner surface. The disclosed barrier fabric(s) and devices utilize an impede-divert-poison strategy that is far more effective than a poison only strategy. The disclosed fabrics and devices utilize this impede-divert-poison strategy with impedimentary wales and diversionary pores (openings) while concurrently providing comfort, durability, re-usability, and pleasing aesthetics that appeal to a wide range of users.

Specifically disclosed are parasitic Acari barrier fabric(s) adapted to impede parasitic Acari movement, trap parasitic Acari, and/or exterminate parasitic Acari thereon or therein. The fabric includes an outer face formed from open mesh construction having evenly spaced openings (pores) formed thereon that are adapted for passing parasitic Acari from outside the fabric to inside the fabric, each opening having a diameter ranging from 3 to 5 mm; an inner face spaced apart from the outer face, the inner face is breathable and configured for moisture vapor transmission from a wearer's skin therethrough but is impenetrable to parasitic Acari passed to the inside of the fabric; and an intermediate spacer that extends between and interconnects the inner face to the outer face to form the parasitic Acari barrier fabric. Each opening of the outer face, the inner face, and intermediate spacer forms individual compartments inside the fabric configured to impede parasitic Acari movement, trap and/or exterminate parasitic Acari therein.

In certain aspects, the evenly spaced openings of the outer face have a density ranging from 1 to 9 openings/cm$^2$.

In certain aspects, the intermediate spacer has a length ranging from 0.5 mm to 3.0 mm in a direction extending from the inner face to the outer face.

In certain aspects, the intermediate spacer is formed of V needle stitch construction.

In certain aspects, each yarn in the intermediate spacer has an angle of intercept ranging from 45° to 85°.

In certain aspects, the inner face is formed of pillar inlay stitch construction.

In certain aspects, the inner face has a moisture vapor transmission rate ranging from 0.020 to 2.0 kPa s/m under ambient conditions.

In certain aspects, the fabric has an overall thickness ranging from about 0.5 to 10 mm in a relaxed state.

In certain aspects, at least one of the outer face, inner face, and intermediate spacer are treated with an acaricide, and in this aspect, the acaricide is microencapsulated.

In certain aspects, at least any two of the outer face, inner face, and intermediate spacer are treated with an acaricide, and in this aspect, the acaricide is microencapsulated.

In certain aspects, each of the outer face, inner face, and intermediate spacer are treated with an acaricide, and in this aspect, the acaricide is microencapsulated.

In certain aspects, the fabric further includes a tubular body configured for donning on a wearer's limb.

In certain aspects, the tubular body is a gaiter.

In certain aspects, the fabric is a puttee configured for wrapping around a wearer's limb or appendage.

Embodiments of the invention can include one or more or any combination of the above features and configurations.

Additional features, aspects and advantages of the invention will be set forth in the detailed description which follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as it is claimed. The accompanying drawings are included to provide a further understanding of the invention, and are incorporated in and constitute a part of this specification.

BRIEF DESCRIPTION OF THE DRAWINGS

These and other features, aspects and advantages of the present invention are better understood when the following detailed description of the invention is read with reference to the accompanying drawings, in which.

DETAILED DESCRIPTION

The present invention will now be described more fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention. Like reference numbers refer to like elements throughout the various drawings.

Figure 1:
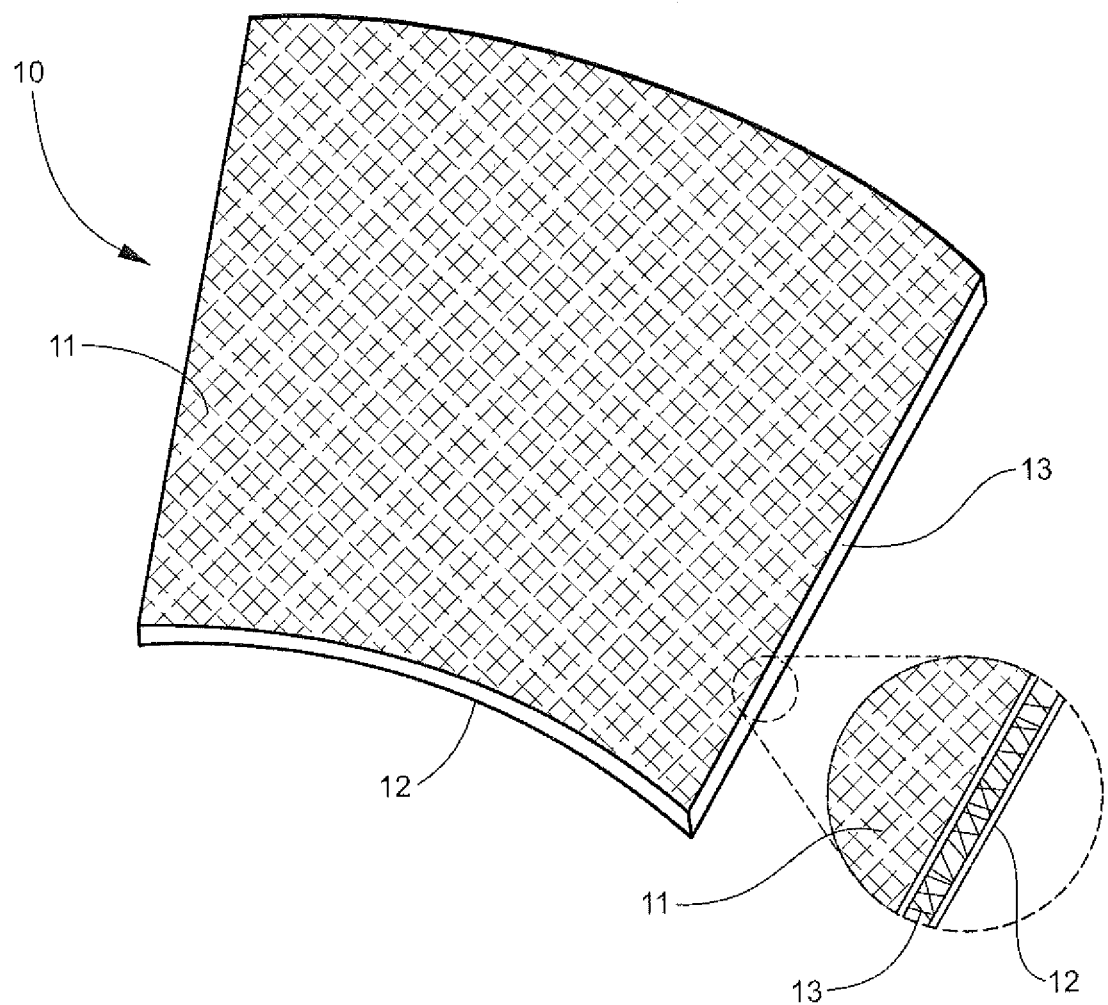
FIG. 1 is a perspective view of the parasitic Acari barrier fabric.
Figure 3:
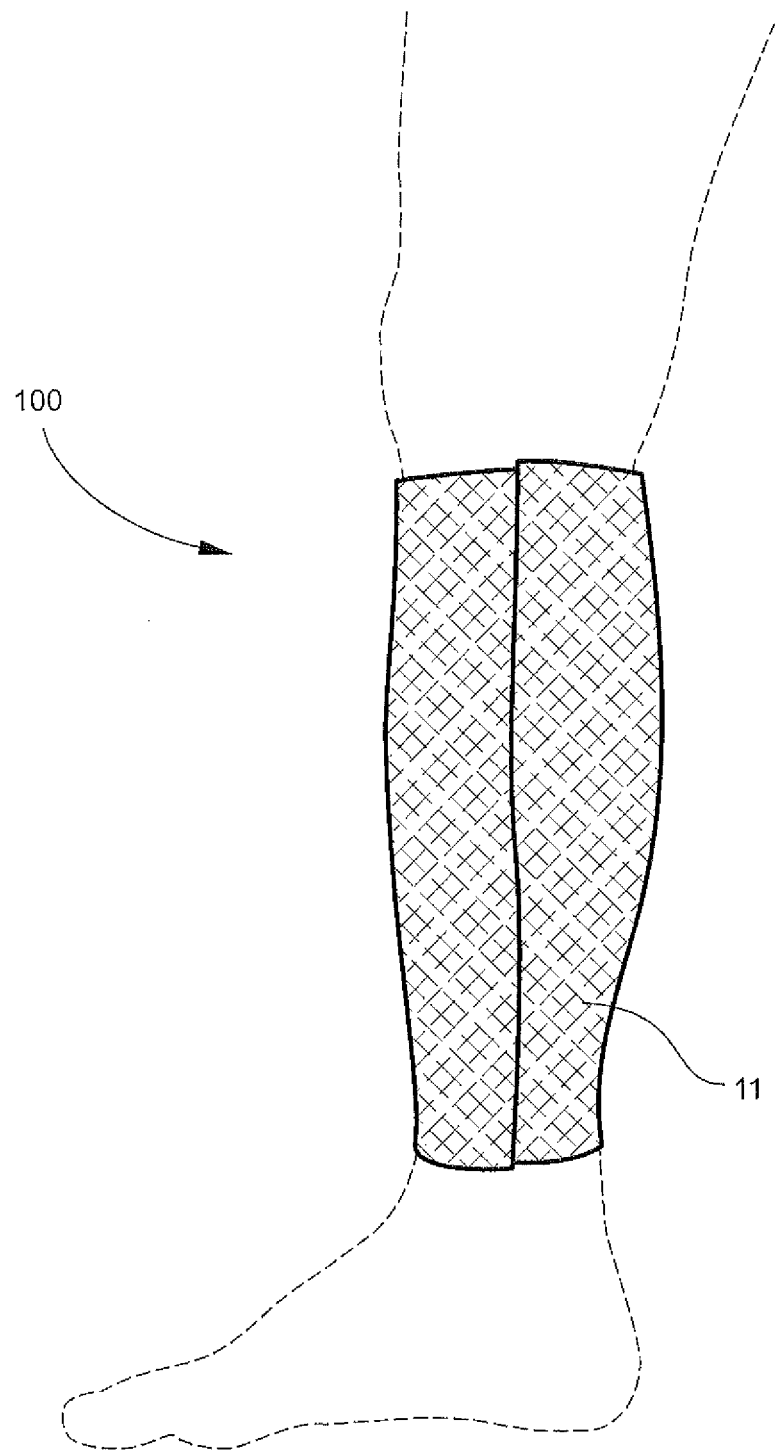
FIG. 3 is a perspective view of a gaiter formed from the Acari barrier fabric.
Figure 4:
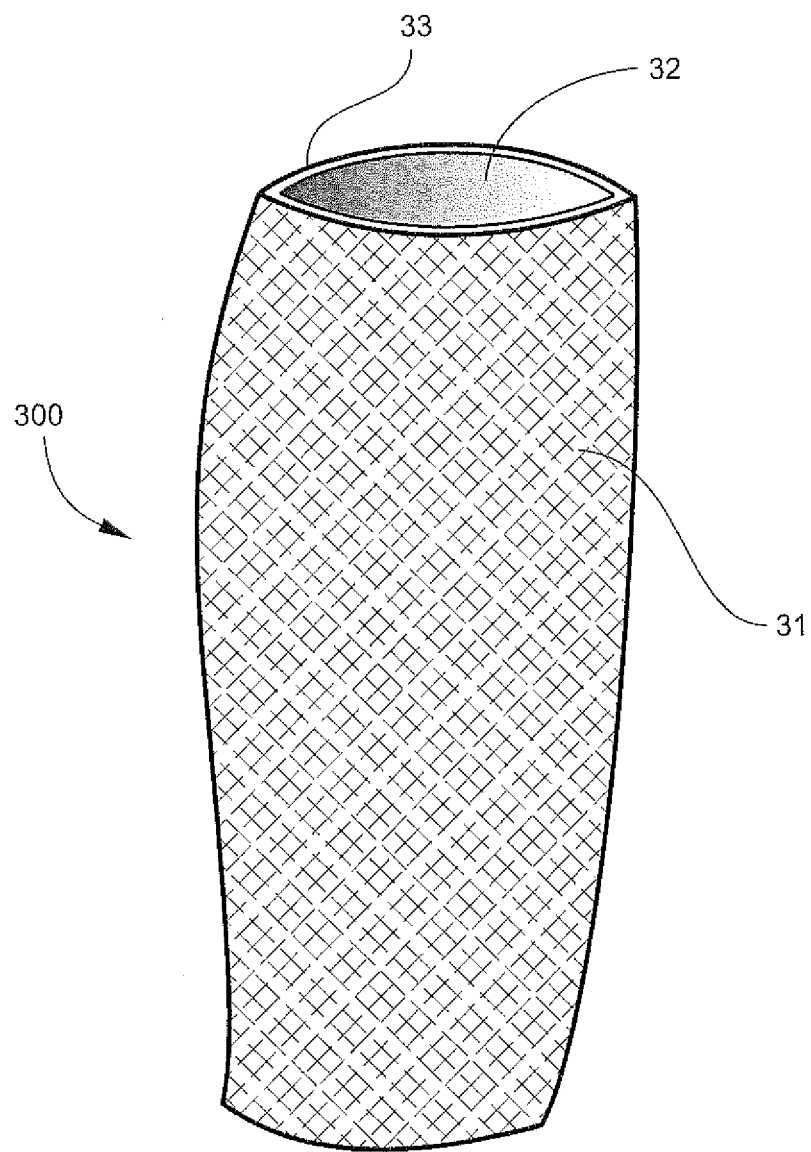
FIG. 4 is a perspective view of an alternative gaiter formed from the Acari barrier fabric.
Figure 5:
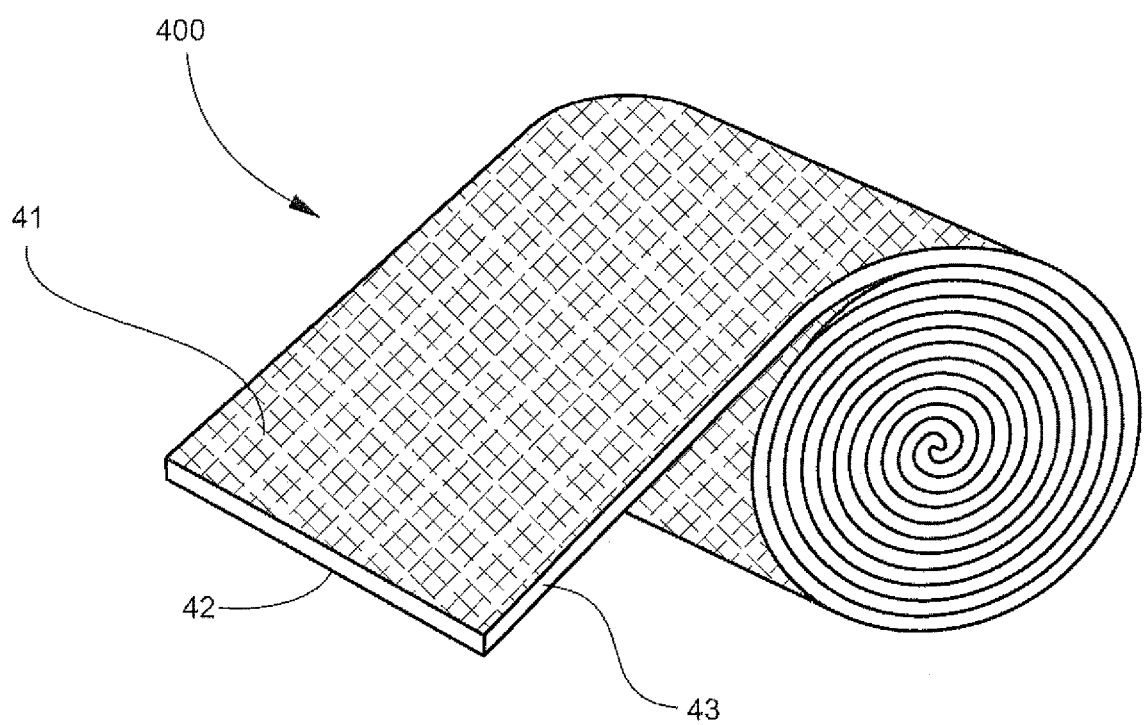
FIG. 5 is a puttee formed from the Acari barrier fabric.
Figure 6:
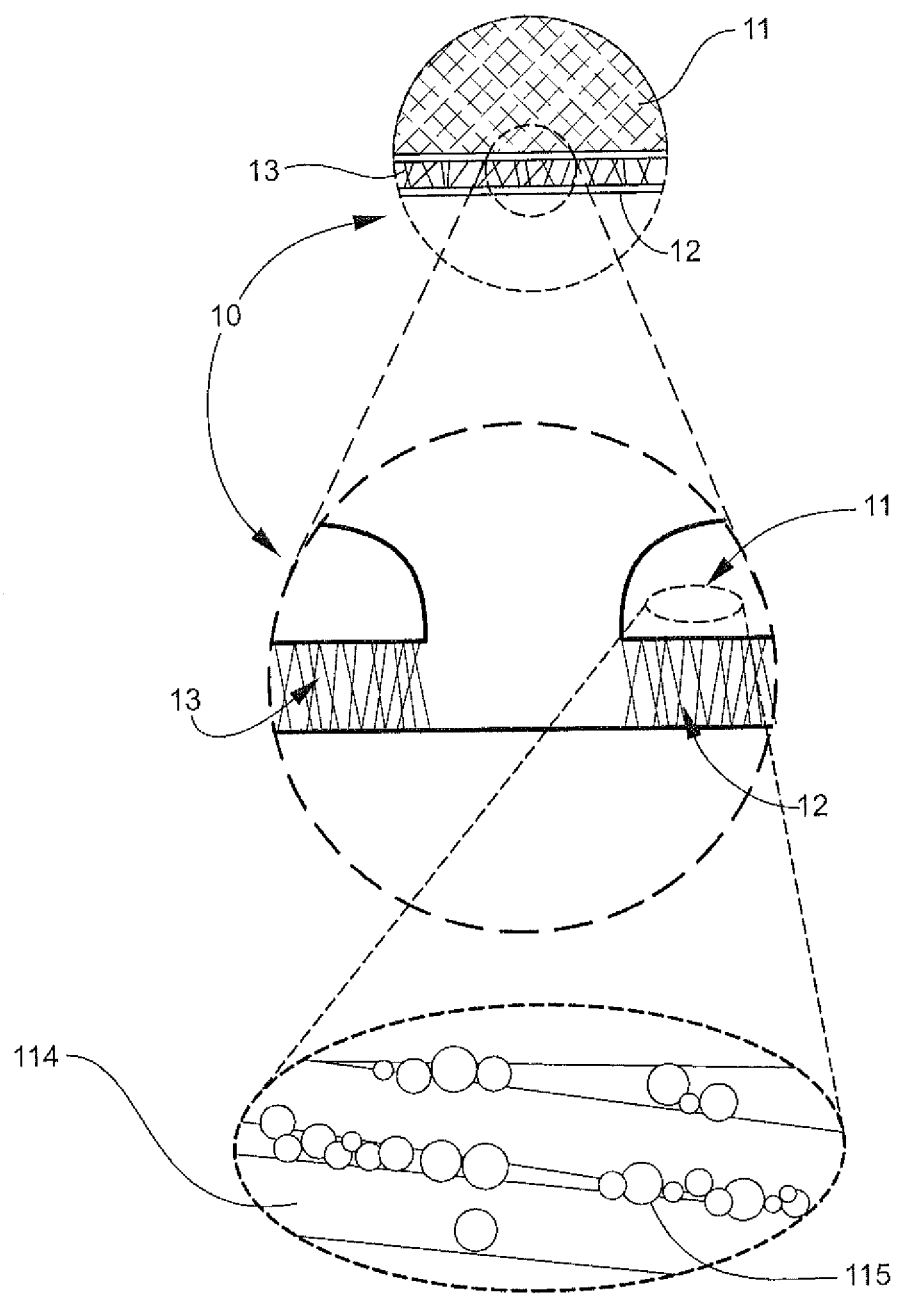
FIG. 6 is a magnified cross-sectional view of the Acari barrier fabric pretreated with a microencapsulated acaricide with a suitable textile binder.

Referring now specifically to the drawings, a parasitic Acari barrier fabric 10, is illustrated in FIGS. 1 and 6. In certain aspects, the barrier fabric 10 fabric may form a gaiter 100, 300 or a puttee 400 as shown in FIGS. 3-5. In certain aspects, the parasitic Acari barrier fabric 10 is treated with an acaricide which may be applied either during manufacture or post-manufacture by the user, which may kill and/or enervate the parasitic Acari.

While the acarine barrier fabric 10 can be formed in any desired width or length, the acarine barrier fabric 10 (and gaiter 100) shown in FIGS. 1 and 3 is about 51 cm wide and 31 cm high and is formed into a conical frustum during manufacture. The parasitic Acari barrier fabric 10 includes two opposing faces 11, 12 and an intermediate spacer 13 that separates and interconnects the faces 11, 12, as described in further detail below. The parasitic Acari barrier 10 can also be formed as a tubular body 300 or in a roll for use as a puttee 400 as shown in FIGS. 4 and 5 respectively.

Figure 2:
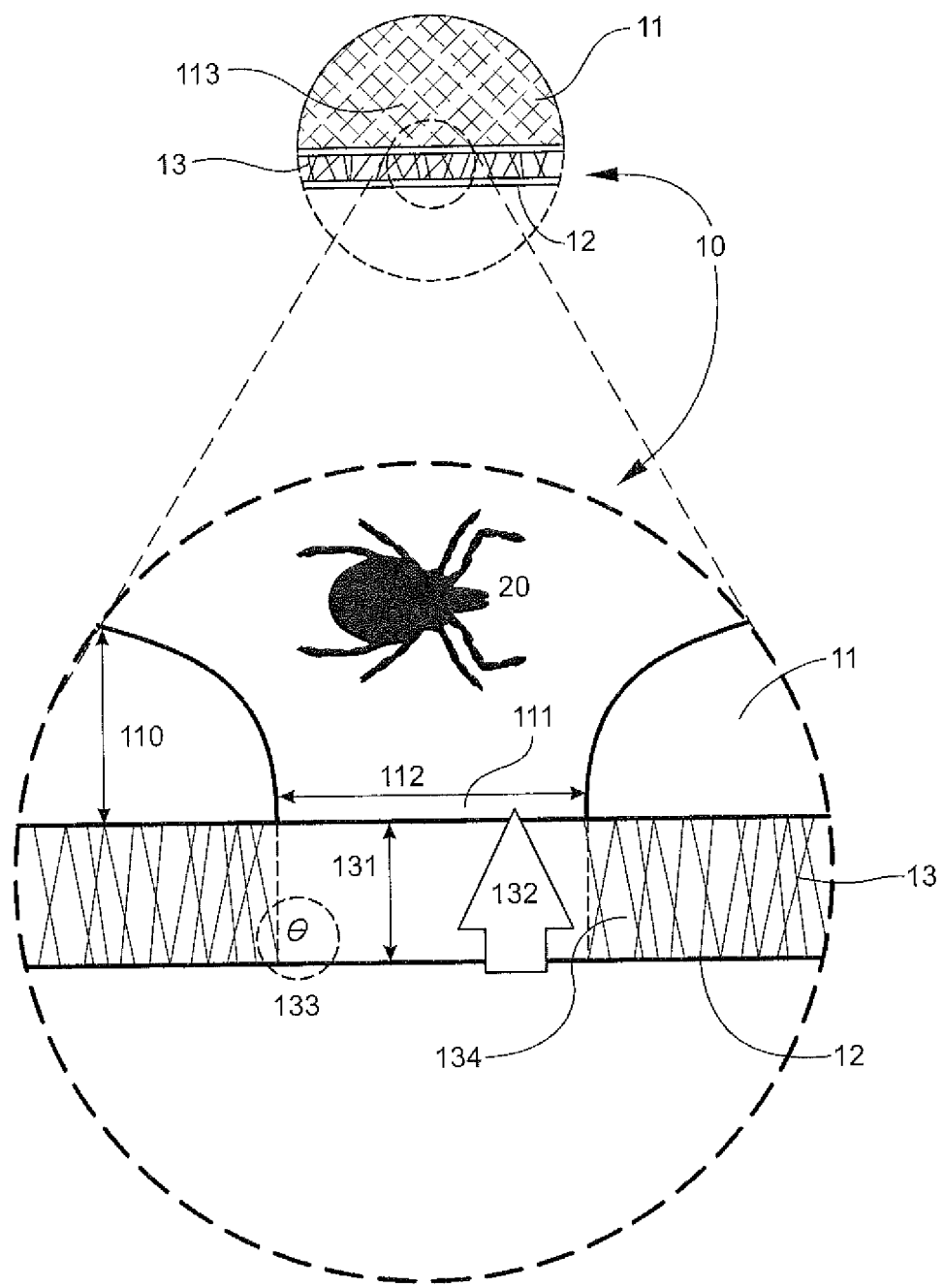
FIG. 2 is a magnified cross-sectional view of the parasitic Acari barrier fabric.

As shown in FIG. 2, the outer face 11 is knitted in an open mesh and includes pores 111 (openings) that allow for parasitic Acari entry and exploration in the fabric. The pores 111, generally created by wale distortion in the knitting, combined with the spacial depth created by the spacer fabric 13 are attractive areas of exploration for the Acari, which slows Acari ascent while advantageously and concurrently exposing parasitic Acari to more of the applied acaricide. Similar to pores 111, knitting underlaps and inclined overlaps of the wales 110 also provide physical impediments that further slow the instinctive upward climb of the parasitic Acari and further expose them to greater amounts of the acaricide.

While the spacer 13 provides breathability, its main function is to provide an attractive diversionary space to the target parasitic Acari so that they ingest more acaricide.

The inner face 12 of the fabric 10 is impenetrable to the parasitic Acari while concurrently providing the wearer with a smooth, nonabrasive surface, thus allowing for the disclosed fabric, gaiter, and/or puttee to be worn over bare skin if so desired. The inner face 12 is knitted such that it is impenetrable by these Acari, yet allows breathability. Breathability of the inner face 12 is particularly important for attracting Acari into the pores 111 and spacer area 13 with the body odor of the wearer.

The acarine barrier fabric 10 is formed using any suitable fabric forming technology such as weaving, various knitting techniques such as, for example, warp knitting and weft knitting, non-woven, stitching, or a combination of these techniques. The outer face 11, the inner face 12, and the intermediate spacer area 13 can be constructed using any suitable organic or inorganic monofilament or multifilament yarn such as polypropylene, polyester, polyethylene and nylon. Preferably, the structure should provide some stretch, whether mechanical or elastomeric, in the width-wise direction, and facilitate conforming the acarine barrier fabric 10, gaiter 100, 300, and/or puttee 400 around an appendage of the wearer.

The parasitic Acari barrier fabric 10, gaiter 100, 300, and/or puttee 400 shown in FIGS. 1 and 3-5 can be treated during manufacture with finishes to provide additional Acari repellency or to improve the functionality or enhance the wrap wearing experience for the wearer.

More specifically, the preferred embodiment of the acarine barrier fabric 10 is constructed of monofilament or multifilament polyester yarns on a double needle bed warp raschel knitting machine. The acarine barrier fabric 10 is preferably constructed using an open-mesh knitting on outer face 11, a pillar and inlay stitch on the inner face 12 and a 3 or 5 needle V in the spacer 13. The parasitic Acari barrier fabric 10 weighs between 50-450 $gm^2$, and more preferably between 200-300 $gm^2$. The parasitic Acari barrier fabric 10 has a nominal thickness when not compressed or under tension of approximately 1.0-4.0 mm.

Referring to FIG. 2, a magnified cross-sectional view of the parasitic Acari barrier fabric 10 is shown. Shown in approximate proportion to the Acari barrier fabric 10 is an exemplary parasitic Acari (e.g., an adult, female *Ixodes scapularis*) 20.

The elements shown of the outer face 11 are wale height 110, pore 111 (including pore diameter (or opening diameter) 112), and pore density 113. The elements shown of the spacer 13 are spacer height 131, airflow 132 as measured by air resistance, spacer yarn arrangement 133 as measured by the angle θ, and spacer yarn diameter 134. The inner face 12 is also shown.

The object of the parasitic Acari barrier fabric 10 is to divert and impede Acari so that their exposure time to the applied acaricides is maximized. Acari, when exploring a mammalian body, are attracted to mammalian $CO_2$, body odor and body warmth. The three variables of the outer layer 11 (wale height 110, pore diameter 112, and pore density 113), the four variables of the spacer layer 13 (spacer height 131, airflow 132, spacer yarn arrangement 133 and spacer yarn diameter 134) in conjunction with the qualities of the inner layer 11 form an effective diversionary and impedimentary apparatus, which attracts, impedes, and kills parasitic Acari.

Wale height 110 is a function of outer layer yarn diameter, desired pore diameter 112 and desired pore density 113. There is no reason not to maximize wale height 110 since wale height serves to lengthen the distance the parasitic Acari must travel across the acaricidally-treated fabric. Yet wale height 110 is both determined, as well as limited by, the desired pore diameter 112 and pore density 113. Wale height 110 will vary depending on the target parasitic Acari from 0.10 mm to 15 mm, and in the preferred embodiment between 0.5 and 2.0 mm.

Pore diameter 112 is determined by the size of the target Acari. In general pore diameter 112 is between 50% and 500% of the target Acari body diameter. Since there is great variation in the size of target parasitic Acari-0.19 mm (larvae of *Trombicula alfreddugesi*) to 3.0 mm (adult *Dermacentor variabilis*)-pore diameter 112 may vary from 0.10 mm to 15 mm. In the preferred embodiment pore diameter 112 is between and 3 mm and 5 mm.

Pore density 113 is the number of pores in fixed area, generally a square centimeter. While parasitic Acari barriers generally have pores of equal size, parasitic Acari barriers with pores of different sizes are possible and anticipated here. In the preferred embodiment, where pore diameter 112 is equal across the fabric and between 3 mm and 5 mm, pore (opening) density 113 is between 1 and 9 pores (openings) per $cm^2$.

Spacer height 131 of the parasitic Acari barrier is sized in proportion to the target Acari body height, ranging from 0.1 mm (larvae of *Trombicula alfreddugesi*) to 1.5 mm (adult *Dermacentor variabilis*). In a preferred embodiment, spacer height is between 0.5 mm and 3 mm.

Airflow 132 through the spacer layer 13, inner layer 12 and outer layer 11 is important in both transferring and retaining body odor, $CO_2$ and body warmth (moisture vapor transmission), which attract the parasitic Acari to the pores of the acaricidally-treated fabric. In the preferred embodiment airflow 132 as measured by fabric air resistance is between 0.020 and 2.0 kPa s/m at ambient conditions.

Spacer yarn arrangement 133 affects the perceived attractiveness of the spacer layer 13 to the target acarines. In the preferred embodiment spacer yarn arrangement 133, as measured by the angle θ, is between 45° and 85°.

Spacer yarn diameter 134 affects both the perceived attractiveness of the spacer layer 13 to the target Acari as well as airflow. In the preferred embodiment spacer yarn diameter will range from 0.03 mm to 0.25 mm for monofilament and between 0.3 mm and 0.85 mm for multifilament yarns.

Referring now to FIG. 4, a circular knit acarine gaiter 300 (tubular body or tubular sleeve) is shown, with the same preferred constructions described of the fabric (i.e., outer face, inner face, and intermediate spacer positioned there between) disclosed above. The acarine gaiter 300 includes an outer face 31 of an open mesh construction, an inner face 32 of tight weave and a spacer area 33 that both separates and interconnects the two faces 31, 32, as shown in FIG. 1. Instead of being wrapped around the limb, the gaiter 30 is pulled onto (donned on) the limb.

Referring now to FIG. 5, an elongate knit acarine barrier fabric is shown in the form of a narrow fabric or puttee 400, with the same preferred constructions described above. The puttee 400 includes an outer face of open mesh 41, an inner face of tightly woven fabric 42 and a spacer area 43 that both separates and interconnects the two faces 41, 42, as shown in FIG. 1.

Referring now to FIG. 6, in one preferred embodiment, any of the fibers of the inner face, outer face, and spacer may be treated with an acaricide. For example, in a preferred embodiment, all of the fibers 114 of the Acari barrier fabric 10, gaiter 100, 300, and/or puttee 400 are treated during manufacture with a microencapsulated acaricide 115 and a suitable textile binder.

In certain additional aspects, the fabric 10, gaiter 100, and/or puttee 400 may further include hook and loop fasteners that further aid in wrapping and fixing the fabric, gaiter, and/or puttee to a wearer.

Working Examples

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric.

Test Description

Travel rates of nympal stage blacklegged ticks (*Ixodes scapularis*) were measured on (1) plain, 100% cotton khaki pants versus (2) an exemplary parasitic barrier fabric (referred to as "Lymeez 3D" in FIGS. 7 and 8) and subsequently compared. Rates were measured as distance traveled/time.

Test Conditions

The below observations were conducted using laboratory-reared, pathogen free ticks (Lot 0216) held at 23° C. and 95% Room humidity (RH) under 14/10 conditions (i.e., 14 hours of light versus 10 hours of dark conditions per day).

During the test, subjects wore either (1) plain, 100% cotton khaki pants or (2) a gaiter made from the untreated parasitic barrier fabric (i.e., a barrier not treated with acaricide) placed over plain, 100% cotton khaki pants. Subjects' legs were held at a constant angle of about 700 relative to the floor. The laboratory-reared, pathogen free ticks (Lot 0216) were subsequently placed at the bottom the plain, 100% khaki pants (25 ticks) and gaiter (25 ticks) and were allowed to move freely thereon for three minutes. The tick's finishing position was marked after 3 minutes, and a straight line measurement (mm) was obtained between each tick's starting and finishing positions on the plain, 100% cotton khaki pants and gaiter respectively.

Results

Figure 7:
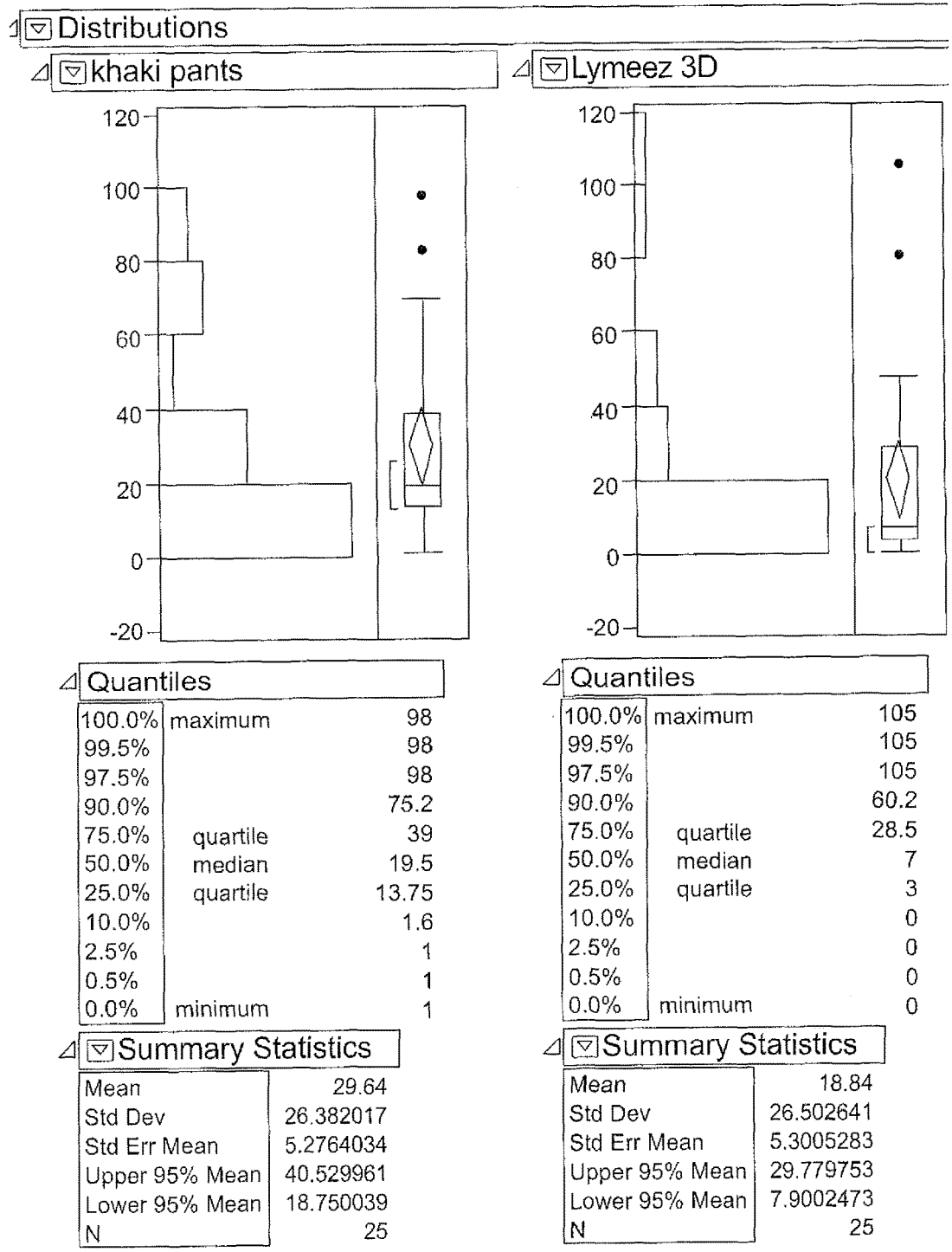
FIG. 7 depicts two separate data sets obtained when allowing pathogen free ticks to move freely on plain, 100% khaki pants or on an exemplary untreated gaiter for a three minute time period.
Figure 8:
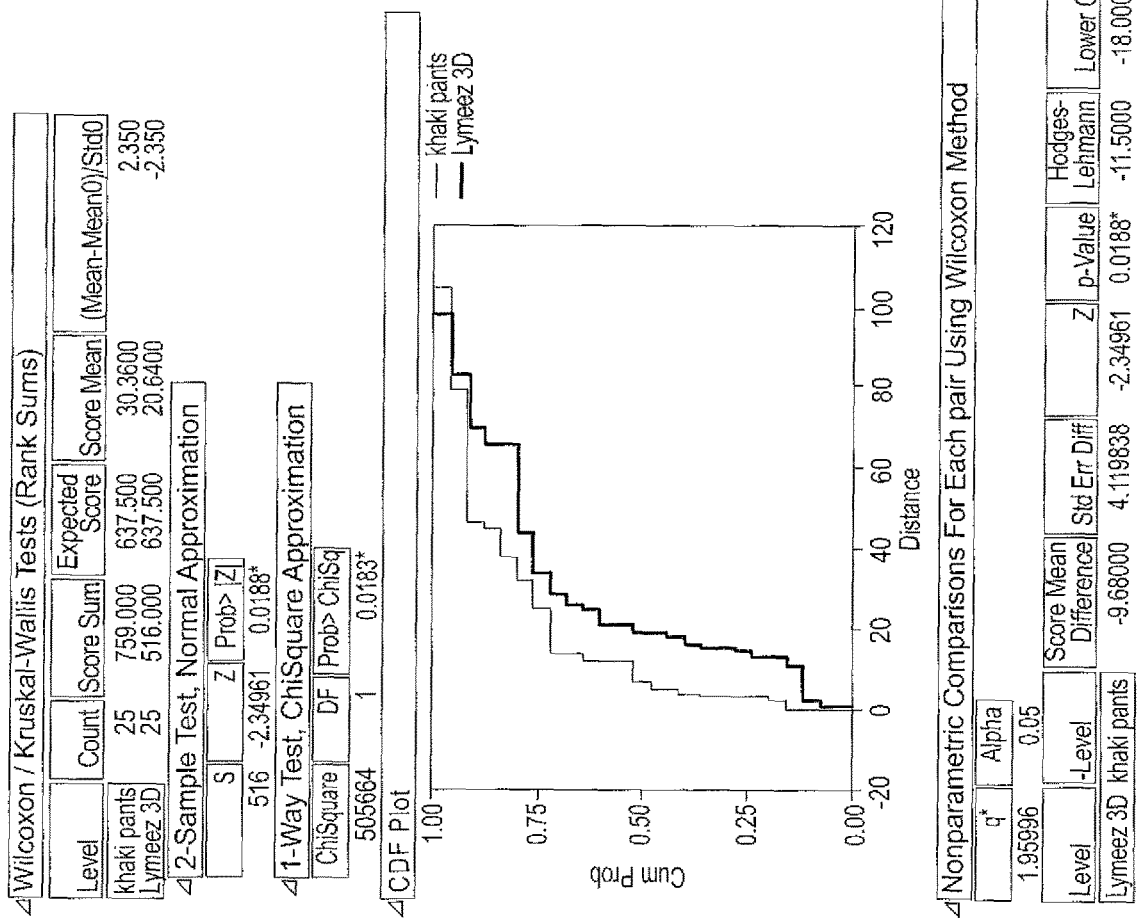
FIG. 8 depicts Wilcoxon statistical analysis obtained from the two separate data sets in FIG. 7.

FIG. 7 provides distribution data of for tick movement placed on the plain, 100% khaki pants and the gaiter respectively after 3 minutes. (Values in the bar graph of FIG. 7 correspond to millimeters traveled in 3 minutes.) FIG. 8 further provides Wilcoxon statistical analysis of the data collected during the above mentioned test. Using the Wilcoxon statistical analysis, a p-value of 0.0188 for the two-sided test was obtained when comparing the medians of the two data sets. As further shown in FIGS. 7 and 8, the medians of the two data sets are statistically, significantly different. The gaiter used in the above described test impeded and/or slowed tick movement roughly three times greater than tick movement observed on the plain, 100% khaki pants (median of 7 versus 19.5).

The foregoing description provides embodiments of the invention by way of example only. It is envisioned that other embodiments may perform similar functions and/or achieve similar results. Any and all such equivalent embodiments and examples are within the scope of the present invention and are intended to be covered by the appended claims.

What is claimed is:

1. A parasitic Acari barrier fabric adapted to impede parasitic Acari movement, trap parasitic Acari, and/or exterminate parasitic Acari thereon or therein, the fabric comprising:

(a) an outer face formed from open mesh construction having evenly spaced openings formed thereon that are adapted for passing parasitic Acari from outside the fabric to inside the fabric, each opening having a diameter ranging from 3 to 5 mm;

(b) an inner face spaced apart from the outer face, the inner face is breathable and configured for moisture vapor transmission from a wearer's skin therethrough but is impenetrable to parasitic Acari passed to the inside of the fabric; and (c) an intermediate spacer that extends between and interconnects the inner face to the outer face to form the parasitic Acari barrier fabric, wherein:

each opening of the outer face, the inner face, and intermediate spacer forms individual compartments inside the fabric configured to impede parasitic Acari movement, trap and/or exterminate parasitic Acari therein;

the evenly spaced openings of the outer face have a density ranging from 1 to 9 openings/cm$^2$;

the intermediate spacer has a length ranging from 0.5 mm to 3.0 mm in a direction extending from the inner face to the outer face; and the intermediate spacer is formed of V needle stitch construction.

2. The parasitic Acari barrier fabric of claim 1, wherein each yarn in the intermediate spacer has an angle of intercept ranging from 45° to 85°.

3. The parasitic Acari barrier fabric of claim 1, wherein the inner face is formed of pillar inlay stitch construction.

4. The parasitic Acari barrier fabric of claim 2, wherein the inner face has a moisture vapor transmission rate ranging from 0.020 to 2.0 kPa s/m under ambient conditions.

5. The parasitic Acari barrier fabric of claim 4, wherein the fabric has an overall thickness ranging from about 0.5 to 10 mm in a relaxed state.

6. The parasitic Acari barrier fabric of claim 5, wherein at least one of the outer face, inner face, and intermediate spacer are treated with an acaricide.

7. The parasitic Acari barrier of claim 6, wherein the acaricide is microencapsulated.

8. The parasitic Acari barrier fabric of claim 5, wherein at least any two of the outer face, inner face, and intermediate spacer are treated with an acaricide.

9. The parasitic Acari barrier of claim 8, wherein the acaricide is microencapsulated.

10. The parasitic Acari barrier fabric of claim 5, wherein each of the outer face, inner face, and intermediate spacer are treated with an acaricide.

11. The parasitic Acari barrier of claim 10, wherein the acaricide is microencapsulated.

12. The parasitic Acari barrier fabric of claim 1, wherein the fabric further comprises a tubular body configured for donning on a wearer's limb.

13. The parasitic Acari barrier fabric of claim 1, wherein the tubular body is a gaiter.

14. The parasitic Acari barrier fabric of claim 1, wherein the fabric comprises a puttee configured for wrapping around a wearer's limb or appendage.

* * * * *